United States Patent [19]

Almenara

[11] Patent Number: 4,478,996
[45] Date of Patent: Oct. 23, 1984

[54] PROCESS FOR THE PREPARATION OF 4-HYDROXY-2-METHYL-2H-1,2-BENZO-THIAZINE-3-CARBOXAMIDE-1,1-DIOXIDES

[75] Inventor: Manuel A. Almenara, Barcelona, Spain

[73] Assignee: Medichem, S.A., Barcelona, Spain

[21] Appl. No.: 472,831

[22] Filed: Mar. 7, 1983

[30] Foreign Application Priority Data

Apr. 16, 1982 [ES] Spain .................................. 511.472
Jan. 11, 1983 [ES] Spain .................................. 518.908
Jan. 11, 1983 [ES] Spain .................................. 518.909

[51] Int. Cl.$^3$ .................. C07D 401/12; C07D 279/02
[52] U.S. Cl. ..................................................... 544/49
[58] Field of Search ........................................... 544/49

[56] References Cited

U.S. PATENT DOCUMENTS 3,868,367 2/1975 Zinnes et al. ......................... 544/49

OTHER PUBLICATIONS

Cram and Hammond, "Organic Chemistry," McGraw-Hill Book Co., 2nd Ed., (1964) New York, p. 316.

*Primary Examiner*—John M. Ford
*Attorney, Agent, or Firm*—Scully, Scott, Murphy & Presser

[57] ABSTRACT

A process for the preparation of 4-hydroxy-2-methyl-2H-1,2-benzothiazine-3-carboxamide-1,1-dioxides, of the formula:

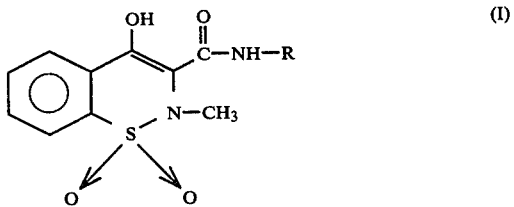

(I)

in which R may be phenyl, aryl substituted with halogen (Cl, Br or I) or with $C_1$–$C_6$ alkyl groups, 2, 3 or 4-pyridyl or pyridyls substituted with halogen (Cl, Br or I) or with $C_1$–$C_6$ alkyl groups, 5-methyl-isoxazolyl or 2-thiazolyl.

In the process a $C_1$–$C_6$ alkyl 4-hydroxy-2-methyl-2H-1,2-benzothiazine-3-carboxylate 1,1-dioxide is reacted with a magnesium derivative of formula:

R-NH-Mg-X in which X is halogen, preferably Br and R is the same as defined for formula (I). The compounds produced by the described process have analgesic and antiinflammatory properties.

4 Claims, No Drawings

PROCESS FOR THE PREPARATION OF 4-HYDROXY-2-METHYL-2H-1,2-BENZOTHIAZINE-3-CARBOXAMIDE-1,1-DIOXIDES

FIELD OF THE INVENTION

This invention relates to a process for the preparation of 4-hydroxy-2-methyl-2H-1,2-benzothiazine-3-carboxamide-1,1-dioxides, compounds having analgesic and antiinflammatory properties and the following formula:

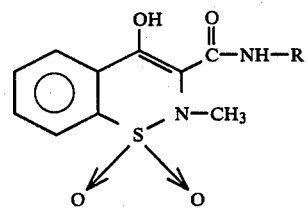

in which R may be phenyl, aryl substituted with halogen (Cl, Br or I) or with $C_1$-$C_6$ alkyl groups, 2, 3 or 4-pyridyl or pyridyls substituted with halogen (Cl, Br or I) or with $C_1$-$C_6$ alkyl groups, 5-methyl-isoxazolyl or 2-thiazolyl.

Among these products there is 4-hydroxy-2-methyl-N-(2-pyridyl)-2H-1,2-benzothiazine-3-carboxamide-1,1-dioxide, of formula:

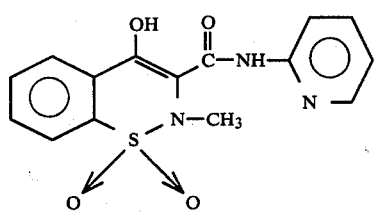

which has therapeutical properties making it particularly interesting.

SUMMARY OF THE INVENTION

The object of the invention is a process for the preparation of the said compounds. The process is characterised essentially in that an alkyl 4-hydroxy-2-methyl-2H-1,2-benzothiazine-3-carboxylate 1,1-dioxide of formula:

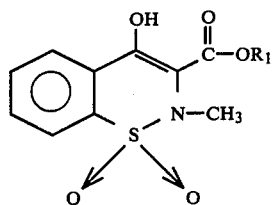

in which $R_1$ is a $C_1$-$C_6$ alkyl group, is reacted with a magnesium derivative of formula:

R—NH—Mg—X  (IV)

in which X is halogen, preferably Br, and R is the same as defined for formula (I). The reaction is carried out in a solvent inert to the reaction at temperatures between 0° and 130° C., until the reaction is almost complete. The intermediate obtained is hydrolysed in an acid medium to give the compound of formula (I), which is recrystallised thereof.

The 4-hydroxy-2-methyl-N-(2-pyridyl)-2H-1,2-benzothiazine-3-carboxamide-1,1-dioxide of formula (II) is prepared, according to the invention, by reacting 4-hydroxy-2-methyl-2H-1,2-benzothiazine-3-carboxylate, 1,1-dioxide of formula (V) (when $R_1$ in formula (III) is -$CH_2$-$CH_3$) with 2-aminopyridyl-magnesium bromide of formula (VI)

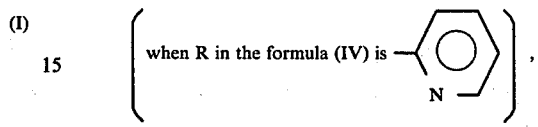

in a solvent inert to the reaction. Subsequent hydrolysis in an acid medium of the intermediate obtained leads to the preparation of the compound of formula (II) according to the following reaction scheme:

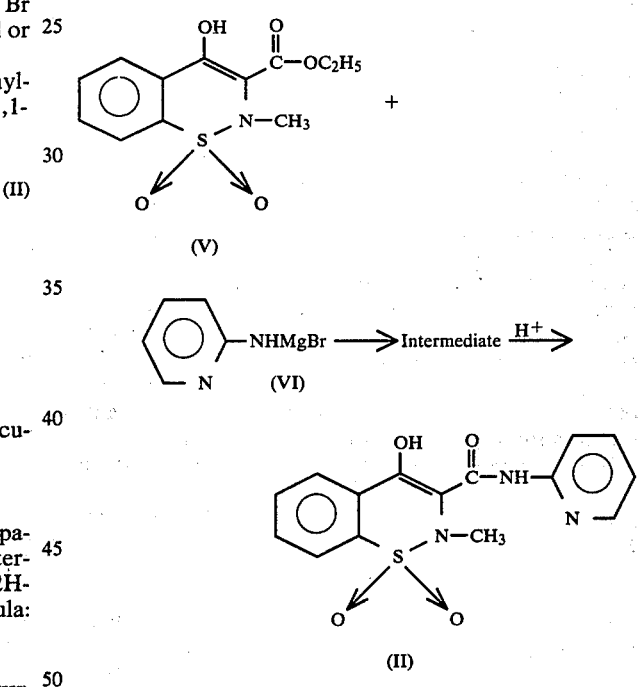

The reaction is carried out, preferably, between 0° and 130° C., by stirring the products (V) and (VI) in a xylene-tetrahydrofurane (THF) mixture for from 1 to 8 hours in an inert atmosphere. The temperature may be, for example, the reflux temperature.

The starting product (V) may be prepared by the processes described in J. Org. Chem. 2241 (1965) and U.S. Pat. No. 3,501,466 and the product (VI), not described up to date, by a process analogous to that described in VOGEL'S "Text-book of practical organic chemistry", page 1124, Fourth Edition, according to the following scheme:

$C_2H_5Br + Mg \longrightarrow C_2H_5MgBr$

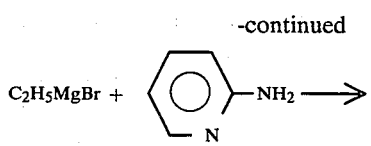

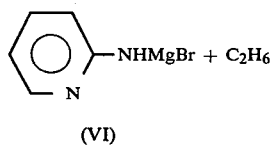

(VI)

EXAMPLE 1

(a) There is placed in a three mouthed flask, provided with an $N_2$ inlet, a reflux coolant and an additional funnel, 1 g (0.04 moles) of Mg, 3.5 ml of ethyl bromide (0.04 moles) and 25 ml of THF and the mixture is stirred at room temperature. The reaction is exothermic and after the reflux due to the reaction itself, it is heated for 10 minutes. Thereafter the solution is cooled and 4.0 g (0.043 moles) of 2-aminopyridine in 25 ml of THF are added dropwise over 15 minutes and stirring is continued for 30 minutes after the addition.

(b) There is placed in a three mouthed flask, provided with an $N_2$ inlet, a reflux coolant and an addition funnel, 5.7 g of the starting product of formula (V) in 100 ml xylene and the mixture is heating to boiling. Thereafter there is added the solution of the product of formula (VI), prepared in the above Example, dropwise over 30 minutes, with reflux being maintained. At the end of the addition, the mixture is stirred with reflux for 2 hours.

During this time a yellow gum forms. After the 2½ hours, the solution is allowed to cool and decanted. The residue is hydrolysed with 1N HCl, the yellow gum becomes a crude solid which is filtered, dried and suspended in $H_2O$ with stirring for 30 minutes. A yellow precipitate is formed and filtered off. 3.3 g of (II) are obtained, m.p. 198°–200° C. (Yield=50%). Recrystallisation in isopropanol gives an analytical sample.

Water content according to the Karl Fisher method: 0.1%. Infra red spectrum in KBr tablet with approximate band in $cm^{-1}$ 3340, 1635, 1580, 1530, 1440, 1355, 1305, 1185.

EXAMPLE 2

(a) There is placed in a three mouthed flask, provided with an $N_2$ inlet, a reflux coolant and an addition funnel 1 g (0.04 mole) of Mg; 3.5 ml (0.04 mole) of ethyl bromide are placed in the addition funnel in 20 ml of tetrahydrofurane, the solution is added dropwise over the Mg for about 25 minutes, the mixture is stirred after the addition is terminated for 10 minutes at room temperature and then heated for 30 minutes at 50° C. After the mixture has cooled, 4 g (0.043 mole) of 2-aminopyridine dissolved in 20 ml of tetrahydrofurane are added and the mixture is stirred for 15 minutes after the addition.

(b) There is dissolved in a 250 ml three mouthed flask, provided with an $N_2$ inlet, reflux cooland and addition funnel, 5.42 g of methyl 4-hydroxy-2-methyl-2H-1,2-benzothiazine-3-carboxylate in 50 ml xylene at 100° C. The previously prepared magnesium solution is added dropwise over 30 minutes over the latter solution, followed by heating for 1½ hours under reflux in an oil bath. The mixture is allowed to cool and the solvent is removed by decantation. The intermediate obtained is a gum to which there is added 100 ml of 1N HCl, followed by stirring for 45 minutes and filtration. A crude product is obtained and is suspended in 80 ml of water with stirring and a yellow solid precipitates. This is collected by filtration.

Recrystallisation of the yellow solid in dichloromethane-methanol gives 4 g of product, m.p. 198°–200° C. The solid is 4-hydroxy-2-methyl-N-(2-pyridyl)-2H-1,2-benzothiazine-3-carboxamide-1,1-dioxide.

Infra red spectrum in KBr tablet with approximate band in $cm^{-1}$ 3340, 1635, 1580, 1530, 1440, 1355, 1305, 1185.

EXAMPLE 3

(a) There is placed in a 100 ml three mouthed flask provided with $N_2$ inlet, reflux coolant and addition funnel, 1 g (0.04 mole) of Mg; 3.5 g (0.04 mole) of ethyl bromide in 20 ml tetrahydrofurane are placed in the addition funnel, are added dropwise over about 25 minutes over the Mg, at the end of the addition the mixture is stirred at room temperature and then heated to 50° C. for 30 minutes. After the mixture has cooled, 4 g (0.043 moles) of aniline dissolved in 20 ml tetrahydrofurane are added dropwise over 20 minutes. At the end of the addition the mixture is stirred for 15 minutes.

(b) There are dissolved in 250 ml three mounted flask provided with an $N_2$ inlet, reflux coolant and addition funnel, 5.7 g of ethyl 4-hydroxy-2-methyl-2H-1,2-benzothiazine-3-carboxylate in 50 ml xylene at 100° C. The previously prepared Grignard's reagent solution is added dropwise to the latter solution over 30 minutes, followed by heating for 1½ hours in an oil bath under reflux. The solution is allowed to cool and the solvent is decanted off. The intermediate obtained is a gum to which there is added 100 ml 1N HCl, followed by stirring for 45 minutes, filtering to give crude 4-hydroxy-2-methyl-2H-1,2-benzothiazine-3-carboxyanilide-1,1-dioxide. Recrystallisation in dichloromethane-methanol gives 2.1 g (30% yield) of pure product, m.p. 210°–213° C. Recrystallisation in isopropanol gives an analytical sample.

EXAMPLE 4

(a) There is placed in a 100 ml three mouthed flask provided with an $N_2$ inlet, reflux coolant and addition funnel, 1 g Mg (0.04 mole); 3.5 ml of ethyl bromide (0.04 mole) in 20 ml of tetrahydrofurane are placed in the addition funnel. The solution is added dropwise over the Mg over about 25 minutes, the mixture is stirred at the end of the addition for 10 minutes at room temperature and is then heated for 30 minutes at 50° C. After the mixture has cooled 4.2 g (0.043 moles) of 3-amino-5-methyl-isoxazol, dissolved in 20 ml tetrahydrofurane, are added. After the addition, the mixture is stirred for 15 minutes.

(b) There are dissolved in a three mouthed flask, provided with an $N_2$ inlet, reflux coolant and addition funnel, 5.7 g of ethyl 4-hydroxy-2-methyl-2H-1,2-benzothiazine-3-carboxylate in 50 ml xylene at 100° C. The previously prepared magnesium solution is added dropwise over 30 minutes over this latter solution, followed by heating under reflux for 1½ hours in an oil bath. The solution is allowed to cool and the solvent is decanted off. The intermediate obtained is a gum to which there is added 100 ml 1N HCl. The mixture is stirred for 15 minutes and filtered to give a grey coloured crude 4-hydroxy-2-methyl-N-(5-methyl-isoxazolyl)-2H-1,2-benzothiazine-3-carboxamide-1,1-dioxide. Recrystallisation in dichloromethane-methanol gives a pure product with m.p. 250°–252° C.

What I claim is:

1. A process for the preparation of 4-hydroxy-2-methyl-2H-1,2-benzothiazine-3-carboxamide-1,1-dioxides wherein an alkyl 4-hydroxy-2-methyl-2H-1,2-benzothiazine-3-carboxylate 1,1-dioxide of formula

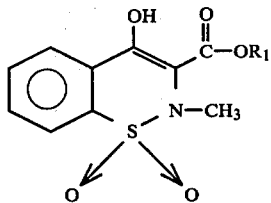

(III)

in which $R_1$ is a $C_1$–$C_6$ alkyl, is reacted with a magnesium derivative of formula:

R—NH—Mg—X    (IV)

in which X is halogen, and R may be phenyl, aryl substituted with halogen (Cl, Br or I) or with $C_1$–$C_6$ alkyl groups, 2, 3 or 4 pyridyl or pyridyls substituted with halogen (Cl, Br or I) or with $C_1$–$C_6$ alkyl groups, 5-methyl-isoxazolyl or 2-thiazolyl, the reaction being carried out in a solvent inert to the reaction at temperature between 0° and 130° C., until the reaction is almost complete, after which the intermediate is hydrolysed in an acid medium and the product obtained, of the formula:

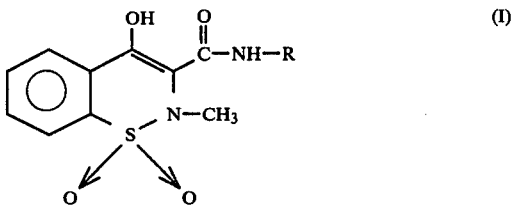

(I)

in which R is as defined hereinbefore, is recrystallised.

2. The process of claim 1, wherein ethyl 4-hydroxy-2-methyl-2H-1,2-benzothiazine-3-carboxylate, 1,1-dioxide of formula (V) is reacted with 2-amino-pyridyl-magnesium bromide of formula (VI) to give 4-hydroxy-2-methyl-N-(2-pyridyl)-2H-1,2-benzothiazine-3-carboxamide-1,1-dioxide.

3. The process of claim 1 or 2, wherein the inert solvent consists of a mixture of xylene-tetrahydrofurane.

4. The process of claim 3, wherein the hydrolysis is carried out with the use of normal hydrochloric acid.

* * * * *